United States Patent [19]

Tan

[11] Patent Number: 5,217,455
[45] Date of Patent: Jun. 8, 1993

[54] LASER TREATMENT METHOD FOR REMOVING PIGMENTATIONS, LESIONS, AND ABNORMALITIES FROM THE SKIN OF A LIVING HUMAN

[76] Inventor: Oon T. Tan, 1 Marlborough St., Boston, Mass. 02116

[21] Appl. No.: 743,797

[22] Filed: Aug. 12, 1991

[51] Int. Cl.⁵ .............................................. A61B 17/36
[52] U.S. Cl. ............................................ 606/9; 606/2; 606/3; 606/13
[58] Field of Search ........................... 606/9, 2, 3, 13; 128/898

[56] References Cited

U.S. PATENT DOCUMENTS

| | | | |
|---|---|---|---|
| 4,316,467 | 2/1982 | Muckerheide | 606/9 |
| 4,718,416 | 1/1988 | Nanaumi | 606/9 |
| 4,854,320 | 8/1989 | Dew et al. | 606/9 X |
| 5,000,752 | 3/1991 | Hoskin et al. | 606/9 |
| 5,057,104 | 10/1991 | Chess | 606/9 |
| 5,059,192 | 10/1991 | Zaias | 606/9 |

FOREIGN PATENT DOCUMENTS 2151483  7/1985  United Kingdom ............ 606/9

Primary Examiner—Peter A. Aschenbrenner
Attorney, Agent, or Firm—David Prashker

[57] ABSTRACT

A laser treatment method is provided which removes pigmentations, lesions, and abnormalities from the skin of a living human. The methodology comprises a carefully controlled irradiation of the chosen treatment site on the skin of a living human; avoids the creation of cosmetically disfiguring scars; and eliminates the typical hypopigmentation as well as the pitting and other changes in skin texture normally accompanying conventionally known laser treatment techniques.

8 Claims, 1 Drawing Sheet

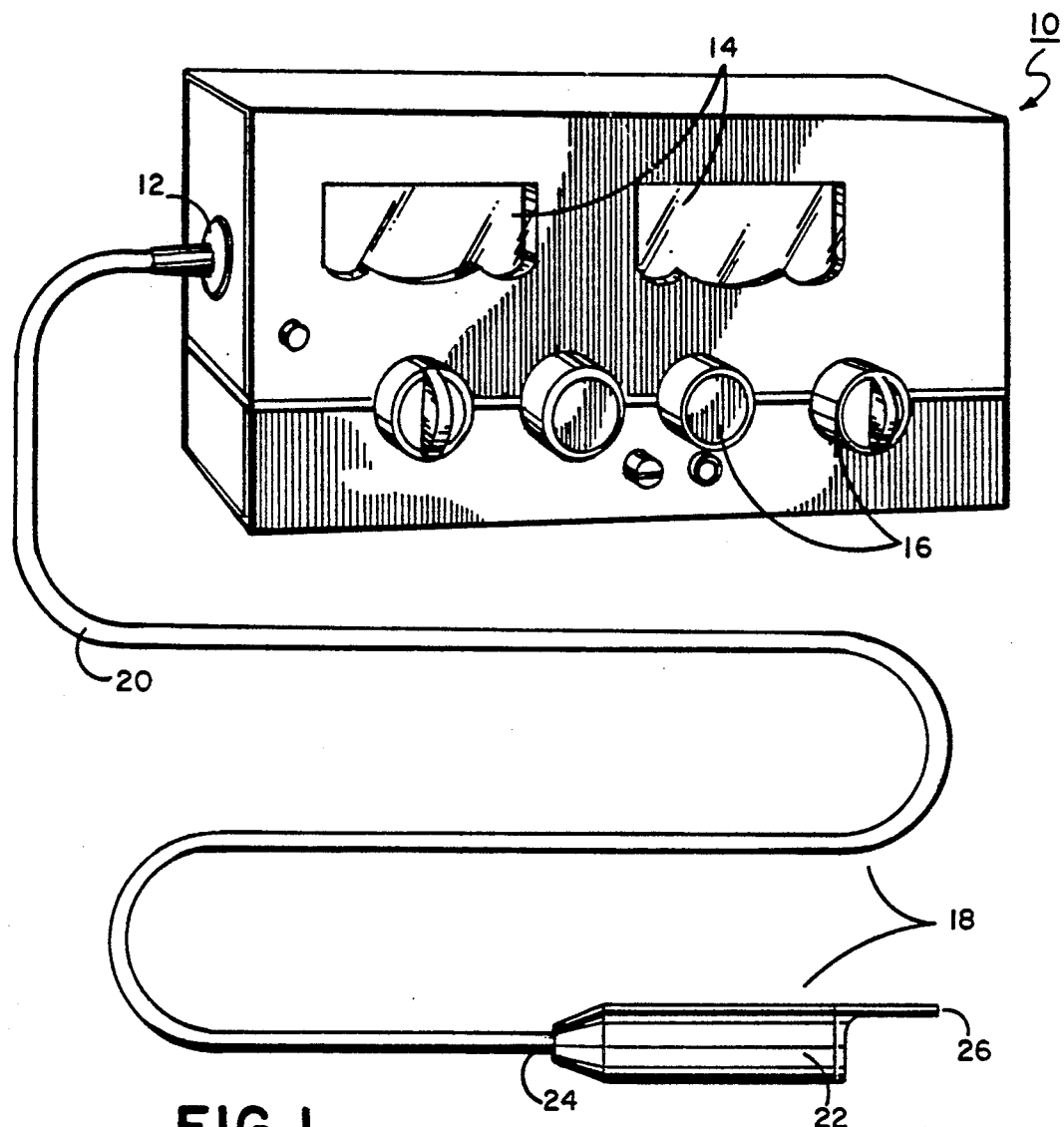
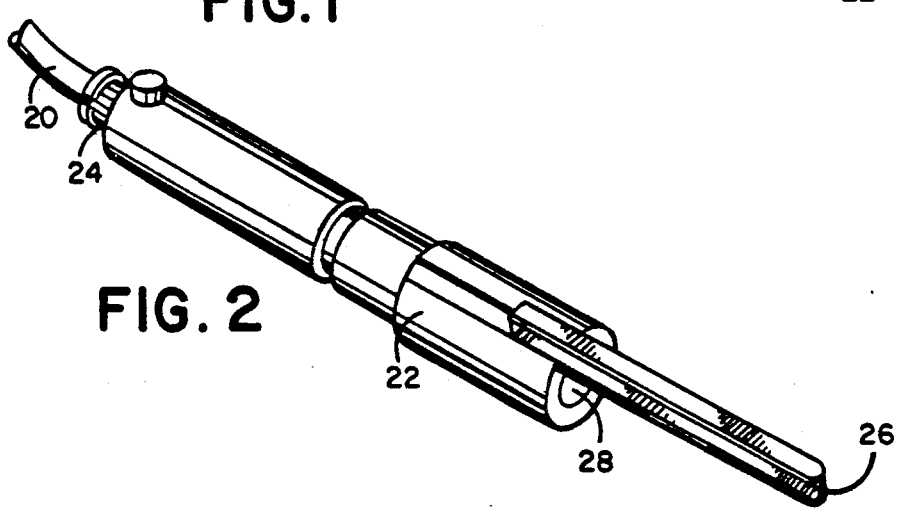

LASER TREATMENT METHOD FOR REMOVING PIGMENTATIONS, LESIONS, AND ABNORMALITIES FROM THE SKIN OF A LIVING HUMAN

FIELD OF THE INVENTION

The present invention is directed to a method for removing pigmentations, lesions, and abnormalities from the skin of a living human using light from a laser and its delivery system; and is particularly directed to the use of the Alexandrite laser apparatus under carefully controlled conditions for the removal of epidermal and dermal tissues as occurs both in nature and by intervention.

BACKGROUND OF THE INVENTION

Among the more common conditions shared by humans generally is the presence of lesions on the skin, many of which are pigmented in one or more colors and some of which are considered abnormal although not always dangerous to the individual. Typical examples of naturally occurring pigmented lesions include freckles; age or liver spots; birth marks; malignant melanomas; nevi (melanocytic, epidermal, vascular, and connective tissue); and lentigines (brown spots on the skin or mucous membrane). In addition, a person's skin may have abnormalities due to vascular lesions which are caused by an abundance of enlarged blood vessels. Common examples of vascular lesions are "port wine" stain birth marks; telangiectasis, a spot formed most commonly on the skin by a dilated capillary or other small blood vessel; and hemangioma, a benign tumor composed of well-formed blood vessels and classified as capillary or cavernous.

In comparison, intervention created pigmented lesions are commonly called "tattoos" and are commonly divided into two different categories: human-caused tattoos and traumatic-inflicted tattoos. Traumatic-inflicted tatoos are created typically as a result of accidents or other mishaps which cause scrapes, abrasions, or lacerations in a manner such that foreign material inadvertently becomes embedded into the skin. During the healing process, the skin becomes pigmented and often scarred as a result. In comparison, human-created tattoos are a popular form of skin decoration and self-expression in many cultures and societies. A common example here in the U.S. is the tattooed sailor; and it has been estimated that as many as 10% of the U.S. general population have tattoos somewhere on the skin of their bodies.

Tattoos are usually pigmented creations and the work of both professional and/or amateur artists who deposit special dyes and/or inks into the skin to create distinctive coloration and patterns which then remain visible over the life of the individual. Tattoos can range in size from a few millimeters in diameter to patterns covering the entire body. In addition, tattoos can also be created using either single or multiple colors. Multiple colored tattoos tend to be done by professional tattooists because of their difficulty and via the use of different colored dyes and inks. The colors employed in a single tattoo can include black, blue, red, yellow, orange, green, purple, and white; the most common colors being black and blue because they are often used to outline the borders of the tattoos themselves. It has also been reported that although many different colors are tattooed into the skin, certain colors tend to fade after one or two years; these are red, yellow, and orange. Thus, the colors which are most commonly found in tattoos of advancing age are usually black, blue, and green. Moreover, the professional tattooist usually creates the tattoo pattern using a vibrating needle which limits the depth into which the pigment(s) is introduced into the skin—usually to the papillary layer of the dermis. In addition, the pigments used by the professional tattoo artists typically include India ink and, increasingly, metallic compounds which have replaced organic materials as the means to produce vivid colors other than blue-black [Slater et al., *Clin. Exp. Dermatol.* 9:167-173 (1984)].

Non-professional tattoos, by contrast, tend to be of a single color, most commonly black or blue. The pigment employed by the amateur tattooist usually is carbon particles (from India ink, soot, or charcoal); and the blue-black appearance of the amateur tattoo is caused by increased scattering at shorter light wavelengths in the dermis because the color of the pigment particles is actually black. In the more crudely created amateur tattoo, the pigment is introduced generally throughout the dermis in an uncontrolled manner because of the hand-held needle traditionally employed for this purpose. Other major differences between the professionally created tattoo and the amateur tattoo include the depth to which the pigment is tattooed into the skin (because professional tattoos tend to be at an even depth lying mainly in the mid-dermis whereas non-professional tattoos tend to vary from site to site); and the density of particles at the tattoo site (professional tattoos typically are dense and evenly distributed whereas amateur created tattoos vary in density from site to site).

It will be recognized and appreciated that many persons at some point in their lives wish to remove pigmented lesions, whether normal or abnormal, from their skin for health and/or cosmetic reasons. Even those individuals who voluntarily choose to create a tattoo on their skin may subsequently choose to undergo treatment designed to remove the tattoo—often because of advancing age, or via a change in lifestyle, or through a new personal relationship. Presently existing modes of treatment may achieve some clearing or lightening of pigmented skin areas but only at substantial risk for the individual because of severe changes to the pigmentation on the skin or the creation of actual scarring of the treated skin area. The risks and severity of the varying problems associated with removing pigmentations and other lesions generally of the skin is best evidenced and demonstrated by the difficulties of removing tattoos.

It is valuable to understand the mechanism of tattoo formation in order to better comprehend the deficiencies and risks presented by conventionally known methods for removing tattoos. An electron microscopic study of amateur created and professionally created tattoos to ascertain the mechanism of tattoo formation has been recently published [Lee P.J. and A. Pawlowski, *Int. J. Vermatol.* 26:453-458 (1987)]. It was found that an acute inflammatory reaction immediately followed the tattooing process; and the various pigment particles deposited in the skin migrated to the dermis through a destroyed basement membrane. Then, as the skin subsequently healed, the basement membrane reformed and the amount of pigment within epidermal cells decreased. The pigment particles, however, were found to be aggregated within dermal fibroblasts in established tattoos. Correlative with this information is the conventional knowledge regarding the absorption spectrum of melanin and the absorption spectrum of charcoal, the two most commonly used materials in tattoos [Wolbarsht et al., *Appl. Optics.* 20:2184–2186 (1981)]. The spectrum of charcoal is representative of both amateur created and blue-black professionally created tattoo pigments (carbon particles from either India ink and/or soot). The relative optical density of melanin has a nearly exponential form in the ultraviolet and visible regions of the spectrum and drops off rapidly with increasing wavelengths. In comparison, the optical density of charcoal remains essentially constant throughout the visible region.

Since the tattoo pigment is inside the skin (i.e., the dermis) destructive modes of treatment to remove this pigment have had to be employed. As is evident, a major problem has been access to the dermal pigment; therefore, the only way it has been possible to remove the pigment(s) without using laser apparatus has been to remove all the skin around the tattoo from the most exterior surface downwards into the deep tissues.

The conventional modes of treatment used for tattoo removal thus presently include: surgical excision and skin graft; dermabrasion; saliabrasion; cryosurgery; and laser light generated by $CO_2$, argon, Nd:YAG, and ruby lasers [Hirshowitz, D.E., *Plast. Reconstr. Surg.* 373–378 (1980); Scutt, R. W. B., Br. *J. Hosp. Med. J.* 8:195 (1972); Manchester, G.H., *Cutis* 7:295 (1971); Clabaugh, F.M., *Plast. Reconstr. Surg.* 55:401 (1975); McDowell, F., *Plast. Reconstr. Surg.* 53:580 (1974); and Groot et al., *J. Am. Acad. Dermatol.* 15:518–522 (1986).

Even the conventional laser treatment methods have generally caused damage to both pigmented and non-pigmented cells in the skin; and the laser treatment of the skin lesions has varied markedly from merely superficial to extremely deep with little attempts to control the amount of tissue destroyed. Moreover, the laser treatment processes known to date cause a change in skin texture. The skin is altered from being smooth, elastic, and mobile to being hard, immobile becoming bumpy, cratered, or pitted. In addition, there is loss of the normal skin markings (normal ridges and valleys) as well as changes in normal skin pigmentation (loss as well as increase in normal skin color). Therefore, the change in skin texture is almost always also accompanied by a change in skin color where the skin of the treated site is no longer normal in color. Instead, the treated skin appears either porcelina-white or mottled with dark pigment, both of these resulting from either loss of all pigment or the implanting of pigment in the dermis instead of the epidermis. All of these changes result from extensive, severe damage induced by the different laser treatment modalities.

Even the ruby laser (the best of the conventionally used laser systems) has been demonstrated to be flawed, deficient, and inefficient for removing pigmentations, lesions, and abnormalities from the skin of a living human. There are many problems concomitant with or caused by the ruby laser system and its various modes of use. In one mode, the ruby laser emits its laser light pulses in short bursts of pulses often called a normal mode pulse train. A pulse train becomes problematic when the pulses are of low power. When this occurs, and provided the pulses are discharged frequently enough, the effect on the tissue will be similar to that of a continuous wave laser. Moreover, instead of destroying the targeted structure with each pulse, because the ruby energy output is low, there is only sufficient energy to partially alter the target. If the pulses are discharged frequently enough then this effect on the target will be cumulative producing an effect which is similar to the continuous wave (cw) laser. Also, due to the characteristics of the ruby laser itself, the intensity of each pulse burst can vary and it is very difficult to control the light energy dose delivered to each treatment site.

In addition, there presently is no convenient or easy way of delivering the laser light beam to the patient. The only way of performing this manipulation at present is by the use of an articulating arm which is not only cumbersome but also easily goes out of alignment. This results in a further decrease of laser energy available to destroy the targeted tissue, thus making the ruby laser system even less efficient for removing abnormal pigmentations. In addition, the ruby laser has been shown to produce severe scarring even when employed in the normal mode.

A second way to operate the ruby laser system is in the Q-switched mode. In this alternative mode of use, a single energy pulse of short duration is delivered by the ruby laser. However, despite the use of Q-switched ruby lasers in clinical studies since the 1960's, the only currently available means of delivering treatment energy pulses is by means of an articulated arm which is not only difficult to align and is bulky, but also creates "hot spots" within the delivered light beam. One reported study revealed that multiple treatments using the ruby laser in the Q-switched mode were required to remove at least 90% of the pigment in the skin. Adverse effects of hyper- and hypo-pigmentation were noted in some patients; and tattooed sites composed of colors other than blue-black were not affected directly but showed a whitening of the skin subsequent to treatment [Read et al., *Br. J Plast. Surg.* 36:455–459 (1983)]. Another study [Taylor et al., *Arch. Dermatol.* 126:893–899 (1990)] reported substantial lightening or total clearing of skin was found in 78% of amateur tattoos and 23% of 13 professional tattoos; but that multiple retreatments were required, transient hypopigmentation was seen in 50% of treated tattoos, and scarring appeared in approximately 6% of patients.

As a consequence, there is major interest in developing alternative laser apparatus and laser delivery systems which could be modified for use in an improved and carefully controlled method for removing pigmentation, lesions, and abnormalities from the skin of a living human. It will be recognized and appreciated that while the development of new laser equipment and new laser delivery systems constitutes one discrete area of technical research, such efforts are meaningfully different and distinct from investigations involving humans directed to developing a clinical process and methodology under carefully controlled operational parameters which would be effective and useable by a dermatologist or other medical practitioner. Equally important, the development of a clinically effective therapeutic treatment using a carefully controlled laser apparatus and laser delivery system which would prevent hypo- and/or hyperpigmentation as well as cratering/pitting and elevation or destruction of dermal and/or epidermal layers of the skin would be generally recognized as a major improvement and advance by practicing dermatologists and clinicians treating patients on a regular basis.

SUMMARY OF THE INVENTION

The present invention constitutes a laser treatment method for removing pigmentations, lesions, and abnormalities from the skin of a living human, said method comprising the steps of:

irradiating on a first occasion a chosen treatment site on the skin of a living human about 1-100 millimeters in diameter with a beam of pulsed light from a laser delivery system, said pulsed laser light having a wavelength from about 600-1,100 nanometers, fluences of about 1-20 Joules per square centimeter, and a pulse duration of about 10-300 nanoseconds;

controlling said irradiation such that the chosen treatment site on the skin of the living human becomes substantially white-gray in color after said laser light irradiation;

allowing the skin at said irradiated treatment site to heal for a time period not less than about 7 days and not more than about 70 days; and then irradiating on at least one subsequent occasion the chosen treatment site on the skin of the living human with another pulsed beam of laser light having a wavelength from 600-1,100 nanometers, fluences of about 1-20 Joules per square centimeter, and a pulse duration of about 10-300 nanoseconds.

BRIEF DESCRIPTION OF THE FIGURE

The present invention may be more easily and completely understood when taken in conjunction with the accompanying drawing, in which:

FIG. 1 is an illustrative view of an unmodified Alexandrite laser apparatus; and FIG. 2 is a detailed view of the delivery system for the Alexandrite laser apparatus of FIG. 1.

DETAILED DESCRIPTION OF THE INVENTION

The present invention is a clinical treatment methodology to be used by clinical dermatologists and other medical practitioners for the removal of pigmentations, lesions, and abnormalities from the skin of a living human. This treatment method employs a laser apparatus and a laser delivery system having specified engineering capabilities able to provide carefully controlled light wavelengths which can be directed at chosen treatment sites on the skin of a living human. Since the methodology intrinsically requires the existence and availability of a laser apparatus having specified capabilities and engineering specifications, descriptive details will be provided herein identifying at least one such laser apparatus which can be modified to provide the specific operating parameters needed in order to perform the treatment methodology efficiently and successfully. Nevertheless, the treatment methodology comprising the manipulative steps of the present invention are not dependent on one particular type or class of laser equipment; and is not restricted to any particular engineering specifications or apparatus designs as such. To the contrary, the present treatment methodology is intended to be and is capable of employing lasers of any type or capacity so long as the specific parameters demanded by the treatment are provided in a predictable and controlled manner. Hence, it will be clearly understood that the present methodology is not dependent on any particular laser equipment or system; and cannot be said to be an outgrowth or derivative of any particular laser apparatus or laser system regardless of how such technology was developed.

The present therapeutic treatment methodology is a dermatological technique suitable for use generally in a variety of different clinical applications. A representative, but non-exhaustive listing of applications and uses for the treatment methodology are identified by Table 1 below.

TABLE 1
Dermatological Applications and Uses (i) Removal of tattoos (professional and non-professional)
(ii) Epidermal and dermal pigment(s) removal
(iii) Removal of melanin pigment from mucosae
(iv) Ablation of skin
(v) Removal of superficial, benign, cutaneous, pigmented lesions
(vi) Removal of foreign matter in the skin including endogenous substances (such as calcium deposits) and exogenous matter (such as lead, gravel, schrapnel, etc.)
(vii) Removal of skin tumors, both benign and malignant A number of major advantages and conveniences are provided by the present treatment method. These include the following:

1. The present methodology is intended to be performed as a series of repeated treatments spaced in time from each other at preselected intervals as chosen by the physician with regard to the individual responses of his patients. Each occasion for treatment (from first to last) will provide an irradiation of the chosen treatment site on the skin of the living human under carefully controlled conditions and include treatment safeguards for exposure based upon the size, condition, and health of the individual's skin. Thus, the therapeutic process is tailored to the individual's particular response to each treatment and medical status; is employed over defined skin areas in limited degree without causing major destruction of the surrounding normal tissues and cells; and provides for periods of skin healing within the planned cycles and timing for the method from beginning to end.

2. The treatment method intends that the targetted treatment site on the skin of the living human be exposed to carefully chosen wavelengths of light energy, energy density and exposure time. If the introductory occasions of irradiation reveal themselves to be insufficient cumulatively to achieve partial or substantial removal of the pigmentation, lesions, or abnormality from the chosen skin site, then the timing, energy density, and duration of light exposure can be increased incrementally as needed on an individual basis until the intervention has been able to achieve the desired goal of selective pigment removal. In this manner, the personal health, safety, and cosmetic appearance of the skin are affected only to the least extent required; and the side-effects of treatment such as scarring or general disfigurement of skin tissues are minimized.

3. The present invention provides a means for delivering the laser energy specifically to targeted zone alone. Because of the particular laser parameters used, the laser light bypasses normal non-targeted skin structures and cells. The laser provides a means by which the destruction of normal skin structures and cells is largely avoided, eliminating loss of skin structures such as hair, sweat glands, pigment-containing cells and the hardening of tissues at the laser exposed site.

4. The present invention also provides for a definitive color change at the skin surface immediately following laser irradiation indicating that the correct treatment dose has been delivered to that area. This is of paramount importance to the clinician. Firstly, the clinician knows exactly the location of where the laser beam has been delivered to the skin. Having a definitive clinical endpoint on the skin surface should prevent the clinician from exposing the area to multiple irradiations (i.e., summation of doses or even missing areas of tattoo altogether). Secondly, the clinician is given a clue by the immediate color change whether the correct dose of laser energy has been delivered to the treatment site.

5. The present treatment method provides means of avoiding and eliminating "whitening" or hypopigmentation as well as hyperpigmentation of the skin which have been the frequent and typical consequence of previously known and conventionally employed laser treatments. The present invention provides criteria by which the blanching and destruction of skin tissues and cells is largely avoided; with the consequence that the typical whitening and abnormal skin appearance is generally eliminated as a concomittant result.

6. The present treatment method also avoids large-scale destruction of the chosen treatment site and the surrounding normal cells and tissues. Immediately following laser irradiation, the focal craters usually formed in the stratum corneum and/or epidermis at each irradiated site; the exudation of tissue fluid from these sites; and the crusting as well as the blistering, are all avoided by this treatment method. Therefore, the potential of developing infection of the treated site, which can also potentially enhance scar formation, is further avoided. Because the tissue injury being induced by this method is specifically confined to the abnormal pigment alone there is no change in skin texture from being smooth to be "bumpy" or even pitted. Similarly, there are no cosmetically disfiguring scars when the methodology is performed in its preferred format.

7. Another major advantage of the present treatment method is that the epidermis in the irradiated area of skin remains intact. This not only decreases the potential risk of infection but also simplifies the management of post operative wound care. Because the skin surface is intact and the treated area does not exude serum from the treated site, forming crusts, this reduces the need to protect the treated skin with dressings for several weeks. Instead, the area need only be protected for between 2–7 days.

In order to provide an accurate, comprehensive, and easily understood description generally and in detail of the present treatment methodology, it is both useful and convenient to focus on a single application or useage for the method. It will be expressly recognized and understood, however, that this focused description is merely representative of all the other intended applications and usages generally, especially those listed within Table 1 previously herein; and that this focused disclosure in detail is merely illustrative of the broad scope encompassed by this treatment method for use by dermatologists and clinicians generally. With this understanding in mind, the detailed description will focus upon the removal of tattoos as the model example and immediate purpose for the treatment method. To achieve this goal, the detailed disclosure will be presented in the following format and sequence: a description of the laser apparatus, hardware modifications, and operation parameters which are necessary for the successful treatment and removal of tattoos; a description of treatment details important for general clinical use and application; a step-by-step protocol for treatment use by the dermatologist or clinician; and a presentation of multiple case histories of treatment with human subjects for the removal of tattoos in accordance with the present invention.

I. Laser Apparatus, Hardware Modifications, and Critical Laser Parameters

Since a useful description of laser apparatus will require a familiarity and understanding of laser equipment generally, its capabilities, and the terminology conventionally understood by laser engineers, a set of defined terms and use conditions are provided hereinafter in order to facilitate comprehension and depth of understanding.

Definitions

Clearance: A value of the laser's ability to disrupt and remove a sufficient amount of dye or ink pigments and to return a tattooed area of skin to near normal appearance as determined by visual inspection and/or photography.

Lightening: An evaluation of the laser's ability to disrupt a sufficient amount of dye or ink pigments in the skin and to significantly reduce the color saturation in a tattooed area of skin as determined by visual inspection and/or photography.

Wavelength: The frequency of the light energy with respect to the spectrum. Wavelengths of radiation in or near the visible region are expressed variously in Angstroms, micrometers, and nanometers. For the present treatment methodology, the wavelengths of light delivered by the laser are limited to the range from 600–1,100 nanometers.

Pulse Duration: The time interval (typically measure, as in this instance, in nanoseconds) over which the laser light beam strikes the chosen treatment site on the skin of the living human. For purposes of the present treatment method, the pulse duration is limited to the range of about 10–300 nanoseconds.

Fluence: The energy density provided by the light beam as applied to the chosen or targetted treatment site on the skin of the living human. The energy density is measured with respect to the surface area and is stated in units of Joules per square centimeter or "$J/cm^2$". The present treatment method intends that a range of fluence from about 1–20 Joules per square centimeter be available for use with the concomittant capability to gradually and incrementally increase the energy density from 1 to 20 Joules per square centimeter at will or as needed.

Spot Size: The size of the chosen or targetted treatment site on the skin of the individual human which is measured in millimeters of diameter. The intended spot size can range from about 1–100 millimeters in diameter with a preferred range of from 1–8 millimeter diameter in most instances initially.

Peak and Average Power: The total amount of energy available from the laser head as determined by the engineering specifications and capabilities of the laser design. For purposes of the present treatment methodology, a peak power of from 5–50 megawatts from the laser head is desirable. A repetition rate of up to 5 Hz is desirable, allowing for an average power of up to 5 watts.

Delivery System: The physical means for delivering the beam of laser light from the laser apparatus to the chosen or targetted treatment site on the skin of the living human patient. This term includes all necessary or desirable equipment, controls, and engineering needed to provide the laser operating parameters critical for successful treatment.

The Preferred Laser Apparatus

The preferred laser apparatus is an Alexandrite laser in the Q-switched mode which provides laser pulses in a time duration in the range of 10-300 nanoseconds; light wavelengths in the red range of the electromagnetic spectrum of about 600-1,100 nanometers; a system for delivering the laser light beam from the laser apparatus to the chosen or targetted treatment site on the skin of the living patient; and, preferably, a handpiece attached to the delivery system for controlling the delivery of the light beam from the laser system to the chosen treatment site on the skin of the patient with a spot size which is variable and ranges from 1-100 millimeters in diameter. The human case histories presented subsequently herein and the individual treatments described there were performed using the Alexandrite laser system provided by Candela Laser Corporation (Wayland, Mass.). The basic Alexandrite laser apparatus was then modified as described herein to meet the critical conditions and operating parameters required by the present treatment methodology. Although any Alexandrite laser apparatus and system can be modified in principle and in designn to provide the necessary parameters and conditions required for use within the present treatment method, it is the individual modifications of the Candela Alexandrite laser and delivery system which are described in detail herein as the representative apparatus used to perform the therapeutic treatment.

The Alexandrite laser delivery system is shown in FIGS. 1 and 2. The apparatus 10 comprises a laser head 12, a high voltage power supply 14, a distilled water circulator (not shown), a control system 16, and a delivery system 18. The laser head contains the cavity mirrors, Pockel's cell, solid-state laser medium (the Alexandrite rod), and two high intensity xenon flashlamps which excite the laser medium. Also incorporated in the laser head is a low power continuous wave red helium-neon laser. The outputs of the Alexandrite and helium-neon lasers are directed into optical components which combine and focus the laser radiation into the delivery system 18.

The delivery system 18 consist of a flexible light guide 20 with a handpiece 22 at its distal end 24. The handpiece 22 incorporates a distance gauge 26 which is placed against the skin of the person to ensure proper focusing of the laser beam on the chosen area of treatment. The output of the red helium-neon laser serves to locate the focal point 28 of the handpiece on the skin; and a footswitch (not shown) is then used to deliver a focused pulse of Alexandrite laser radiation to the chosen treatment site targeted by the helium-neon laser.

The high voltage power supply charges a set of storage capacitors which provide energy to the flashlamps. Depressing the footswitch initiates a trigger pulse which causes the capacitors to discharge through the flashlamps. The resulting flash excites the Alexandrite rod, causing the emission of a pulse of laser energy. The energy of the pulse is determined by the energy stored by the capacitors, which in turn is controlled by the high voltage on the capacitors. A low power DC discharge is maintained in the lamps between pulses by a simmer circuit.

The temperature of the Alexandrite rod must be controlled for efficient lasing to be achieved. Circulation of heated, distilled water around the rod regulates the temperature and also serves to cool the flashlamps. The circulator unit which pumps the heated water through the flashlamp/rod assembly has a reservoir that is maintained at the desired temperature. A display on the circulator allows the temperature of the water to be monitored. The physician controls the fluence (energy density) using a 10-turn knob on the control panel of the high voltage power supply to select the voltage on the capacitors. This control panel is also used to enable or disable the triggering of the laser (by turning on or off the high voltage inverter), and to start the flashlamp simmer current prior to triggering the laser.

The Alexandrite laser apparatus is desirably equipped with interlocks that turn off the high voltage power supply to prevent lasing when the cover of the laser head is opened or when the distilled water level in the circulator reservoir is low. Representative apparatus specifications are provided by Table 2 below.

TABLE 2

| APPARATUS SPECIFICATIONS | |
|---|---|
| Laser Type: | Flashlamp excited Alexandrite laser |
| Wavelength: | 600-1,100 nm ± 10 nm |
| Method of Optical Output: | Lens coupled light guide |
| Mode of Output: | Multimode |
| Operating Mode: | Single pulse operation |
| Maximum Delivered Output Energy: | 1-20 Joules/pulse |
| Spot Size: | 1-100 mm |
| Pulse Characteristics: | |
| Rate: | Single pulse (1.0 Hz maximum) |
| Duration: | 1-300 nanoseconds |
| Energy Source: | Flashlamps |

II. Hardware Modifications and Laser Operating Parameters

Certain laser operating parameters are critical for the successful treatment of tattoos. These include:

a. a pulse duration (exposure time) in the tens to hundreds of nanoseconds range (10-300 nanoseconds);
b. a light wavelength in the red range of the electromagnetic spectrum (600-1,100 nm);
c. average power of 1-20 watts from the laser head;
d. a delivery system for delivering the laser light from the laser to the patient which might take the form of a light-guide, articulating arm, or even a fiber-optic fiber; and
e. a handpiece for delivery of the laser light from the delivery system which can be placed at fixed distances from the skin surface of the patient to ensure that spot size ranging from 1-100 mm in diameter are being delivered.

III. General Treatment Procedures and Preferred Details

Both amateur and professional tattoos can be successfully treated using the Q-switched Alexandrite laser. The colors of tattoo which respond best are black and blue. However, green has also responded well as have orange and yellow colors.

The Alexandrite laser apparatus should be Q-switched to provide pulse durations of from 10–300 nanoseconds, and preferably between 50–200 nanoseconds. The spot size of the laser beam ranges between 1–100 millimeters in diameter and desirably is from 3–5 millimeters in diameter. The light wavelength should be around 760 nanometers. The energy densities used for irradiation treatment should begin in the range from 2.0 to 10.0 Joules per square centimeter, but may be 1–20 Joules per square centimeter on any occasion or as the individual's needs demand.

Specific colors of tattoos (i.e., black, blue, etc.) should be identified, localized, and nominated as test sites. Specific energy densities (Joules per square centimeter) (test energy densities) should be chosen and used to treat these small areas of the tattoo as initial test sites. The skin should either be grayish-white and even slightly reddened immediately following laser exposure of that test area. If the skin retains its normal skin tone after the laser exposure, then the energy density or fluence should be increased by 0.5–1.0 Joules per square centimeter until the skin surface becomes grayish-white and reddened and swollen. This change in skin color should occur immediately (up to ten minutes) after laser exposure. The skin surface (epidermis) should remain intact. If the laser dose is too high, blisters or punctured holes in the stratum corneum or skin surface will appear. This will be accompanied by redness and swelling of the surrounding area at each of the laser irradiated sites will be evident. The laser exposed site should be protected from being traumatized by the application of a small non-adherent dressing. The patient should be asked to return for the next treatment visit at any time between one to ten weeks afterwards for evaluation of the irradiated test site.

At the second or subsequent visit, the test skin area previously irradiated is assessed for:
(a) meaningful color changes (i.e., lightening, clearance, or no change) of the tattoo. A notation should also be made of the color of the immediately adjacent normal skin color;
(b) a skin texture change (i.e., elasticity, rigidity of the skin);
(c) a change in surface skin markings (i.e., the normal surface ridges and valleys of the skin disappear when scarring occurs); and
(d) the presence or absence of adnexae (skin appendages) such as hairs before and after irradiation.

The laser exposed skin color as well as the color change in the tattoo itself should be carefully examined and compared to adjacent normal and non-treated tattoed skin colors. If the skin color in the laser treated area appears abnormal (porcelain white or mottled brown) compared to normal skin color, this suggests that the dose used for the first treatment is too high. By contrast, if the treated area remains totally unchanged then insufficient laser energy has been delivered to the tattoo. In other words, the treated skin site should feel as elastic and mobile as the normal adjacent skin.

The goal of the treatment is to lighten and eventually clear the tattoo with successive and repeated laser treatments; and at the same time, leave the surrounding normal skin intact and unaffected. However, if no change in the color of the tattoo at the test site has been noted at the return visit, then a further test area and test irradiation will be performed (at a higher laser dose (by increasing the energy density of the light beam by 0.5–1.0 Joules per square centimeter). The same process of test site assessment should be performed again as outlined above subsequently at between one to ten weeks following laser irradiation. Evaluation of test sites should continue to be performed using increasing energy densities until substantial lightening and/or clearance of the test site tattoo is achieved.

Note carefully, however, if one or more significant changes in the skin comprising any of the features outlined above are observed, then the energy density should be decreased and additional test site assessments should be performed until the "ideal" treatment dose (i.e., the minimum laser fluence and duration required to produce lightening and/or clearance) is achieved.

Once the correct fluence and duration has been determined (i.e., the best energy density and timed exposure producing lightening of the tattoo with minimal alteration to normal skin) that fluence should be used to treat a large area of the tattoo of the same color in that individual. Separate areas, section by section, of the tattoo are then repeatedly irradiated on multiple occasions until the entirety of the tattoo has been removed.

IV. Step-by-Step Preferred Protocol for Treatment

The following protocol is provided as the best detailed procedure presently available for the removal of tattoos. It will be clearly recognized and understood, however, that this preferred protocol is but a model format for many others which would vary in some details but retain the essential and critical features of the methodology generally.

History and Examination

A careful history should be taken to establish when and by whom the tattoo was placed on the skin of the patient as well as the colors tattooed into the skin. In addition, it should be established whether other treatment modalities have been used at any time previously in an attempt to remove the tattoo. Details of the prior treatment and the modalities used should be documented.

Examination should consist of a description of the actual design of the tattoo, the colors present in the tattoo, and the presence or absence of abnormal skin texture including scars or abnormal pigmentation present in the tattoo. Photographs should be taken of the tattoo prior to irradiation treatment and at each subsequent visit and irradiation treatment session.

Treatment Protocol

Two to three small areas (approximately 1–3 square centimeters of each color, if appropriate) should be delineated on the tattoo. These will be designated as the test site areas. Several test doses (e.g., 2.5, 3.0 Joules per square centimeter) should be used to irradiate the different test sites. The skin should turn white/gray immediately or within ten minutes following laser exposure. If the skin remains unchanged in color when fluences greater than 6 $J/cm^2$ are delivered, the laser output should be checked using an energy meter If the output is correct, then a slightly higher fluence will be required. One should increase the fluence by about 0.5 Joules per square centimeter as necessary and look out for the development of whitening/graying on the irradiated skin. If necessary, fluences of 10–20 $J/cm^2$ may be employed. The typical fluence to be used for the test site should initially be less than 5 or 6 $J/cm^2$ at a spot size of 3–5 millimeters in diameter The epidermis at the treatment site should remain intact after the irradiation exposure.

Following skin irradiation, a topical antibiotic ointment is preferably applied to the treated site and the skin area protected using a non-adherent dressing. Such topical antibiotic ointments include Bacitracin, Neosporin, Polysporin, and Sulphadene. Alternatively, a topical cream such as Vitamin E cream may be used in place of the antibiotic ointment. Daily applications of the topical antibiotic ointment and dressings to the treated site should be advocated for approximately one week or until such time as the discoloration on the skin disappears.

The patient should be scheduled to return anytime between one and ten weeks afterwards for subsequent evaluation of color change (i.e., lightening of the tattoo with minimal change in normal skin color) and alteration in skin texture. A preferred time interval for the return visit is about 3-7 weeks. If the laser irradiated test site appears lightened at the return visit, the lowest dose (fluence) producing the best lightening of the skin should be used to irradiate the same area again as well as other areas of tattoo having the same color using the same laser fluence and pulse duration. However, if one or more of the test sites have been unresponsive to the initial laser test dose, a higher fluence (increased preferably by 0.5-1.0 Joules per square centimeter) should be used at other test sites.

The same regimen of repeated irradiations over multiple visits should be instituted and completed until a satisfactory dose producing lightening of the skin site is established. If no change is observed at the different test sites following one or more exposure using fluences of 5 to 10 Joules per square centimeter, then it is likely that the particular color in the tattoo will be unresponsive to this laser.

Once a satisfactory laser fluence and irradiation exposure has been determined, different sections of the tattoo are then separately irradiated. Those treated skin areas which have lightened in meaningful degree following laser exposure should be irradiated again at one to ten week intervals repeatedly. It is likely that it will be necessary to increase the laser fluence periodically to remove the remnants of the tattoo as it decreases in size and color. Irradiation of the tattoo, section by section, should be repeated until the tattoo is completely cleared In order to achieve this, it may be necessary to increase the laser fluence to as much as 20 Joules per square centimeter on subsequent visits repeatedly.

V. Human Case Reports

Case History No. 1

A 29 year old caucasian male with a professional tattoo on his chest which was tattooed with the words "ROCKY & ROCKY JR" using blue/black ink 9 years previously.

The Alexandrite laser was set at 760 nanometers with a pulse duration in the 50 to 100 nanosecond pulse duration range to cover a spot size of 3 millimeters diameter at fluences (energy densities)) of 2-5 Joules per square centimeter. These operating parameters were used to treat different zones or parts of the tattoo as test sites. It was observed that the skin at the exposed test sites, including the hairs, turned grayish-white immediately after laser irradiation. This was accompanied by the apparent disappearance of the tattoo from the laser exposed site. The surface of the skin (i.e., the stratum corneum) remained intact and the skin surface did not perforate (burst open) immediately following laser exposure.

Within 5 minutes of laser exposure, the grayish/whitening which was presennt on the surface disappeared and the tattoo reappeared at the laser exposed site. Accompanying this reappearance, the laser irradiated site appeared "swollen" (edematous) and reddened.

At the four week follow-up visit, a thorough examination of the irradiated test skin area was made. No significant color change in the laser treated tattoo sites were observed. Another test site was delinated and exposed to 5 J/cm$^2$ using a 3 mm diameter spotsize. The exposed test skin site again turned grayish-white immediately after irradiation which then again disappeared from the treated skin surface about 5 minutes afterwards. The patient was then asked to return three weeks later for the next repeat visit.

At this subsequent three week visit, clearance of the tattoo treated previously at 5 J/cm$^2$ was noted. In addition, the laser treated exposed site appeared slightly lighter than normal skin. Because there were still remnants of tattoo at the treated site, the same skin area was again treated using a fluence of 4 J/cm$^2$. Section by section irradiations of the entire tattoo were then begun.

The tattoo sections responded with lightening to irradiations of 4 and 5 Joules per square centimeter on the initial occasion. Repeat irradiation treatments were then delivered to the same tattoo sections using these same fluences at time intervals ranging between two and six weeks.

The tattoo became lightened with each successive irradiation treatment in sequence, eventually clearing the entirety of the tattoo. The skin at the treated sites retained its normal skin color as well as its normal skin markings and elasticity throughout the irradiation treatment regimen.

Case History No. 2

A 34 year old caucasian male had multiple professional tattoos of several color (green, red, yellow, black, and orange) of 18 years' age on both his arms.

The patient stated that several colors had faded in the first two years after the tattoo was placed. The yellow color faded first followed by the fading of orange and red. At the time of initial treatment, the tattoo was blue-black in appearance.

The Alexandrite laser was used to test the effects of irradiating the green and black sections of the tattoo using fluences of 2, 4, and 5 J/cm$^2$ respectively. The initial response immediately following laser exposure was that the irradiated skin surface turned grayish-white. This was accompanied by swelling of each test site within 1-5 minutes of laser exposure. The grayish-white discoloration disappeared over the next 5-10 minutes, after which time the tattoo reappeared and the laser exposed sites remained swollen. The time taken for the whitening/graying to disappear after laser exposure was longer at the higher fluences, taking up to 20 minutes to disappear.

The best response with lightening was achieved using 4 and 5 Joules per square centimeter on the blue/black tattoo sections at an exposure time of 50-100 nsec. These skin areas have been repeatedly irradiated using the same energy densities and exposure time. Lightening of the tattoo continued with each irradiation treatment in series. In addition, some sections of the tattoo have already been cleaned of pigment leaving the skin at the irradiated site normal both in color and texture..

Treatment of the tattoo, section by section, is presently continuing It is likely that it will be necessary periodically to increase the energy density (possibly up to 20 Joules per square centimeter) as the treatment program progresses, and as the tattoo pigment decreases in amount, and as the pigment aggregates fragment into smaller particles. It is expected that eachh skin section may require up to 15 or 20 repeat irradiation treatments to become completely cleared of the tattoo. A major benefit to the patient of this procedure is that the cleared skin in the treated sections is indistinguishable from the normal adjacent, non-tattooed, skin in that person.

Case History No. 3

Amateur tattoos on both arms, on the back of right hand, and on all four fingers and chest were created 37 and 40 years ago using Indian ink in a caucasian male now 53 years old. The index, middle, and fourth fingers were designated as the initial test sites. The treatment doses and lasers used as well as the follow-up treatments are outlined in Table 3 below.

TABLE 3

FLUENCES USED TO TREAT INDIVIDUAL TATTOOS IN CASE HISTORY NO. 3*

| Date | Index | Middle | Ring | Fifth | Hand |
|------|-------|--------|------|-------|------|
| 3/05 | 4 J/cm$^2$ | N/A | 5 J/cm$^2$ | N/A | N/A |
| 3/26 | 5 J/cm$^2$ | 5 J/cm$^2$ | 5 J/cm$^2$ | 5 J/cm$^2$ | 5 J/cm$^2$ |
| 4/14 | 4 J/cm$^2$ | 4 J/cm$^2$ | 4 J/cm$^2$ | 4 J/cm$^2$ | 4 J/cm$^2$ |
| 5/14 | 5 J/cm$^2$ | 5 J/cm$^2$ | 5 J/cm$^2$ | 5 J/cm$^2$ | 5 J/cm$^2$ |

*Other laser parameters remained constant.
Spot size = 3 mm diameters.
Pulse duration = 50-100 nsec.
Wavelength = 760 nm.
N/A = not attempted.

The tattoos at these individual sites lightened with each irradiation exposure except those skin areas irradiated on the initial visit of 3/05. The fluences employed on that occasion were varied to determine how differences in laser energy density would affect the degree of lightening achieved.

On the initial visit of 3/05, the treated skin turned grayish-white immediately after laser exposure at both 4 and 5 J/cm$^2$ respectively. Then, about 5-7 minutes after irradiation, the grayish-white coloration was replaced by the return of the pigmented tattoo at each of the treated test sites.

At the return visit of 3/26, very little change was seen in the previously irradiated skin sites and the laser fluence used on 3/05 was then increased by 1 J/cm$^2$, while keeping the other laser operating parameters constant. Again, the skin sites irradiated on this occasion turned grayish-white immmediately after laser exposure The patient was then asked to return in 20 days time for the next visit.

At the follow-up visit of 4/14, a few areas of the previously irradiated skin appeared slightly lighter than the adjacent non-tattooed normal skin. Therefore, the laser fluence was decreased to 4 J/cm$^2$ using an exposure time of 50-100 nsec and a spot size of 3 mm in diameter. After treatment, the patient was scheduled to return in 30 days for his next visit.

On the visit of 5/14, however, very little change in color was observed at those skin sites irradiated on 4/14 using the 4 J/cm$^2$ energy density. Therefore, the fluence was again increased to 5 J/cm$^2$ while the other operating parameters of exposure time, spot size, and light wavelength remained the same. Treatment of the tattoo, section by section, was then begun.

It is expected that increases in laser fluence up to 20 J/cm$^2$ will be required to clear the tattoo entirely as it lightens in color. Also, it is likely that multiple treatments involving to 20 return visits will be needed at intervals of 2-10 weeks between each irradiation treatment in order to complete the regimen.

Case History No. 4

An amateur tattoo with the words "JOHN" on the left outer thigh of a 33 year old caucasian female was created 13 to 14 years ago using blue Indian ink. The whole lesion, which was approximately 1.5×3.0 cm, was exposed to light from the Alexandrite laser at 760 nm, 50-100 nsec exposure time, 3 mm diameter spotsize, and a fluence of 5 J/cm$^2$. The skin immediately following laser exposure turned grayish-white, this coloration gradually disappearing after 5-10 minutes and after which the treated sites appeared swollen, raised, and pink. When the tattoo was examined at the second visit six weeks following the initial treatment, the whole tattoo had lightened and thus was retreated using the same laser operating parameters. Laser exposures of the tattoo now continue with return visits for treatment scheduled between two and eight week intervals and with incresing irradiation fluence until the whole tattoo clears completely. It is expected that between 8 and 12 treatments will be required to completely clear the tattoo.

Case History No. 5

A professional tattoo formed as two hands clasped together was placed 30 years ago on the right forearm of a caucasian male now 47 years old. The right side of the tattoo was purposely exposed to laser light from the conventional ruby laser wile the left side on the tattoo was exposed to laser light from the Alexandrite laser. The operating parameters of both laser irradiations were similar; each irradiation used a fluence of 4 J/cm$^2$ and an exposure time of 50-100 nsec.

At the first return visit 4 weeks later, the patient reported that the right side of the tattoo exposed to the ruby laser oozed shortly after initial irradiation; and that the oozing was replaced by crusts on the skin surface within 1-2 days of treatment. The skin crusts persisted for nearly two weeks and then gradually fell off leaving the skin area "whiter" than the normal adjacent skin. By the time of this first return visit (4 weeks after initial irradiation), a lightening of both the right and left sides of the tattoo was observed.

The treatment procedure was then purposely repeated on this first return visit; the right and left sides of the tattoo were again irradiated individually using the ruby laser and Alexandrite laser and the same operating parameter as on the initial treatment occasion. The patient was then asked to return after four additional weeks for his next visit.

On the third visit (8 weeks after initial treatment), the right side of the tattoo exposed to the ruby laser appeared more hypopigmented—that is, whiter in color and more shiny in appearance—than the left side of the tattoo irradiated previously using Alexandrite laser light. In addition, the skin on the Alexandrite laser treated left side was not only completely cleared of the tattoo but also appeared normal both in skin color and skin texture with respect to the untreated skin areas immediately adjacent. However, the Alexandrite laser treated skin was substantially different and in marked contrast to the ruby laser exposed skin which demonstrated a potentially permanent loss of normal skin pigmentation as a consequence of irradiation.

It is of major significance that the left side of the tattoo irradiated with the Alexandrite laser light has apparently cleared completely after only two irradiation treatment occasions; and has left the treated skin area of the patient in a normal condition as to both coloration and texture. It is also noteworthy that the Alexandrite laser treated skin did not cause any oozing of the skin tissue; did not become crusty or hard as a consequence of the irradiation; and did not become either hypopigmented or scarred.

The remainder of the tattoo of the patient will now be treated section by section using only Alexandrite laser light under the earlier described operating parameters. Treatment visits will be scheduled repeatedly at 2-8 week time intervals with increasing irradiation fluence if necessary until the entirety of the tattoo is completely cleared. It is expected that approximately 10-15 treatment occasions will be required to achieve complete clearance of the entire tattoo.

Case History No. 6

A 42 year old caucasian male had a panther professionally tattooed on his left upper arm 25 years earlier. Most of the tattoo was outlined and filled in with blue/black ink. The tip of the panther's tail was irradiated using a fluence of 2.5 Joules per square centimeter for 50-100 nsec using the Q-switched Alexandrite laser while another part of the tail was irradiated using the ruby laser with light at 694 nanometers using fluences of 2.0 and 3.5 Joules per square centimeter for the same time exposure. On the return visit, approximaely six weeks later, very little change was observed in the skin at the Alexandrite laser irradiated area but some lightening of skin was observed at the ruby laser irradiated site. At this return visit also, the right leg and the lower half of the body of the panther tattoo was exposed to light from the Alexandrite laser at a fluence of 4 Joules per square centimeter while the left leg of the panther tattoo was exposed to the ruby laser at a fluence of 4 Joules per square centimeter, both irradiations being of 50-100 nsec exposure time. The patient was then scheduled to return in 4 weeks.

On the occasion of his third visit, a direct comparison of the ruby laser treated skin and the Alexandrite laser irradiated skin was made in detail. Significant lightening was observed at all the treated skin sites However, areas treated using the ruby laser had punctate openings at the surface of each site through which oozed blood and serum. These areas subsequently crusted over; some of this crusting was still evident after ten weeks. By contrast, the skin remained intact at every site exposed to the Alexandrite laser in spite of the fact that the skin turned a grayish white immediately after laser irradiation on each occasion Another difference noted at the third visit was the fact that the ruby laser irradiated site appeared hypopigmented compared to the Alexandrite irradiated sites. These findings suggest that the Alexandrite laser beam penerated deeper into skin than the ruby laser beam. Therefore, because the tattoo pigment most often "aggregates" around dermal vessels in the papillary dermis, the Alexandrite is a more efficient laser for destroying pigment than the ruby laser. This is because some of the ruby laser's energy Will be lost through absorption by more superficial cutaneous structures such as stratum corneum and epidermis. When this happens, very little energy will be left for absorption by structures in the dermis. Moreover, it is evident that short pulses at high powers are needed to fragment dermal tattoo pigment. Because the ruby laser will have lost some of its energy at the surface, it will be less efficient at breaking up the tattoo fragment in the dermis. In order to be able to break up the tattoo pigment, higher doses will be required; and when high doses are used, then more damage will be induced at the skin surface. This damage consequently will heal by scar formation.

This tattoo will now be treated using increasing doses of alexandrite laser light alone at two to eight weekly intervals for an expected 15-20 treatment visits at which time the tattoo will be completely cleared.

The present invention is not to be restricted in form nor limited in scope except by the claims appended hereto.

What I claim is:

1. A laser treatment method for removing a tattoo from the skin of a living human, said method comprising the steps of:
    irradiating on a first occasion a chosen treatment site on the skin of a living human of about 1-100 millimeters in diameter with a beam of pulsed light from a laser delivery system, said pulsed light having a wavelength from about 600-1,100 nanometers, fluences of about 1-20 Joules per square centimeter, and a pulse duration of about 10-300 nanoseconds;
    maintaining said irradiation to disrupt the tattoo on the chosen treatment site on the skin of the living human until a color change endpoint on the skin surface is achieved by said laser light treatment while largely avoiding the destruction of normal skin structures and cells;
    allowing the skin at said irradiated treatment site to heal for a time period not less than about 7 days and not more than about 70 days; and then
    irradiating on at least one subsequent occasion the chosen treatment site on the skin of the living human with another pulsed beam of laser light having a wavelength from about 600 to 1,100 nanometers, fluences of about 1-20 Joules per square centimeter, and a pulse duration of about 10-300 nanoseconds, said subsequent irradiation occasion being repeated as necessary to achieve substantial clearance of the chosen treatment site on the skin.

2. The laser treatment method as recited in claim 1 wherein said irradiation of the chosen treatment site on the skin is controlled to avoid causing whiteness and pitting of the skin.

3. The laser treatment method as recited in claim 1 wherein said irradiation on the first occasion employs a lesser fluence value than said irradiation on said subsequent.

4. The laser treatment method as recited in claim 1 wherein said irradiation on said first occasion employs a greater fluence valve than said irradiation on said subsequent occasion.

5. The laser treatment method as recited in claim 1 wherein said irradiation employs laser light having a wavelength of from 750-800 nanometers.

6. The laser treatment method as recited in claim 1 further comprising additional irradiations on subsequent occasions of the chosen treatment site on the skin of the living human, each of said irradiations employing pulsed laser light having a wavelength of about 600–1,000 nanometers, fluences of about 1–20 Joules per square centimeter, and a pulse duration of about 10–300 nanoseconds.

7. The laser treatment method as recited in claim 1 further comprising applying a topical antibiotic preparation to the chosen treatment site on the skin after each irradiation occasion.

8. A laser treatment method for removing a tattoo from the skin of a living human, said method comprising the steps of:

irradiating on a first occasion a chosen treatment site on the skin of a living human of about 1–100 millimeters in diameter with a beam of pulsed light from a laser delivery system, said pulsed light having a wavelength from about 600–1,100 nanometers, fluences of about 1–20 Joules per square centimeter, and a pulse duration of about 10–300 nanoseconds;

maintaining said irradiation of the chosen treatment site to disrupt the tattoo on the skin of the living human until a color change endpoint on the skin surface is achieved by said laser light treatment while largely avoiding the destruction of normal skin structures and cells;

allowing the skin at said irradiated treatment site to heal for a time period not less than about 7 days and not more than about 70 days; and then irradiating on multiple subsequent occasions the chosen treatment site on the skin of the living human with another pulsed beam of laser light having a wavelength from about 600 to 1,100 nanometers, fluences of about 1–20 Joules per square centimeter, and a pulse duration of about 10–300 nanoseconds, said subsequent irradiation occasions being repeated as necessary to achieve substantial clearance of the chosen treatment site on the skin.

* * * * *